United States Patent [19]

Ewen

[11] 4,116,239
[45] Sep. 26, 1978

[54] ULTRASONIC OXYGENATION INSTRUMENT

[76] Inventor: Sol J. Ewen, 107-21 Queens Blvd., Forest Hills, N.Y. 11375

[21] Appl. No.: 479,549

[22] Filed: Jun. 14, 1974

[51] Int. Cl.² .......................................... R61M 13/00
[52] U.S. Cl. .................................. 128/184; 32/40 R
[58] Field of Search ................. 128/239, 62 A, 24 A, 128/173.1, 184, 187, 172.2, 173.1; 32/40 R, 58, 59

[56] References Cited

U.S. PATENT DOCUMENTS

| 2,623,519 | 12/1952 | Cohen | 128/184 |
| 2,662,523 | 12/1953 | Badan | 128/184 |
| 3,645,255 | 2/1972 | Robinson | 128/62 A |
| 3,698,088 | 10/1972 | Austin | 32/22 |

Primary Examiner—Robert Peshock
Attorney, Agent, or Firm—Michael Ebert

[57] ABSTRACT

An ultrasonic instrument having biological, medical, dental and periodontal applications, the instrument producing a jet of oxygen which may be projected toward diseased tissue or any other site in need of cleansing and oxygenation. The instrument includes a hand-held ultrasonic transducer having a nozzle attached thereto, the transducer being energized by a high-frequency generator. The nozzle is coupled by a flexible tube to a tank of pressurized oxygen, the stream of oxygen passing through the vibrating nozzle being ultrasonically activated thereby to produce a highly reactive jet which may be directed toward the site being treated.

7 Claims, 6 Drawing Figures

ULTRASONIC OXYGENATION INSTRUMENT

BACKGROUND OF THE INVENTION

This invention relates generally to oxygenation techniques, and more particularly to apparatus for producing a jet of ultrasonically-activated oxygen or other fluids for treating periodontal tissue.

Ultrasonic energy is generated by driving an electromechanical transducer with a high-frequency voltage that is converted by the transducer into corresponding mechanical vibrations. The form of the associated electronic circuit is governed by the nature of the application. Thus for ultrasonic cleaning, the power generator is usually of the electronic oscillator-amplifier type providing a continuous wave voltage, whereas for ultrasonic testing, pulsed oscillations are required. The electro-mechanical transducers may be in the form of magnetostrictive or piezoelectric oscillators.

One significant property of ultrasonic energy that renders such vibration especially useful in cleaning, dispersion, emulsification, homogenization and in many other practical applications is cavitation. Cavitation induced by an ultrasonic field at a low energy level acts to degas, whereas at a higher energy level it generates gas bubbles that implode, releasing shock waves of great intensity.

As noted in the text "Ultrasonics" (2nd Edition) by Benson Carlin — McGraw Hill, ultrasonics has several useful applications in medicine and dentistry. Thus ultrasonic diagnostic equipment is capable of locating tumors, while ultrasonically-actuated surgical tools may be utilized to remove tumors. In the field of dentistry, ultrasonic devices may be used to drill, grind and clean teeth.

The application of ultrasonics to the treatment of periodontal disease is of particular interest. As indicated in the text "Ultrasonic Therapy in Periodontics" by Ewen and Glickstein — published by Charles C. Thomas, ultrasonic techniques are useful in scaling, root planing, curettage and overhang removal.

In applying ultrasonics to periodontics, use is usually made of a magnetostrictor encased in a cylindrical handpiece having a small applicator or tip projecting therefrom, the magnetostrictor being energized by a high-frequency generator whereby the resultant ultrasonic vibrations are transferred to the tip. This vibratory motion, in the case of a straight tip, is a simple reciprocatory action. More complex motions are obtained by curved or non-linear tips. Such tips, when applied properly to the tooth surface, are able while undergoing vibration to remove calcarous deposits and necrotic accumulations from the surface, to curet or debride the crevicular wall of soft tissue, to flush out the pocket and to cut tissue.

Because of heat generated in magnetostrictive transducers, it is the present practice to provide a constant flow of water or medicated fluid around the transducer in the handpiece, the water flowing through the handpiece and being expelled from an outlet near the end of the tip. This water flow not only dissipates heat developed in the transducer but it also serves for lavage and to provide a medium for cavitation. The ultrasonically-vibrating tip produces cavitation in the fluid, the cavitating water jet reinforcing the mechanical action and acting concurrently to cleanse and wash the area under treatment.

Inasmuch as the present invention makes use of ultrasonic transducers and generators of the type described in the above-identified Ewen and Glickstein text for periodontal applications, the description of such equipment is incorporated herein by reference.

SUMMARY OF THE INVENTION

The main object of this invention is to provide an ultrasonic oxygenation instrument having biological, medical, dental and periodontal applications, the instrument producing an activated jet of oxygen which may be projected toward diseased tissue or any other site requiring treatment or which may be injected therein.

More specifically, it is an object of this invention to provide an instrument of the above-noted type in which a nozzle attached to a hand-held magnetostrictor and rendered vibratory thereby is coupled to a pressurized source of medical oxygen and functions to emit an oxygen jet which may be directed to a site being treated.

The therapeutic value of oxygenation in the treatment of diseased tissue is well recognized. Because the stream of oxygen passing through the nozzle is subjected to vibratory energy in the ultrasonic range, the oxygen is activated thereby to acquire highly-reactive properties comparable to that of nascent oxygen whereby oxygenation is promoted. And because the jet of activated oxygen is pressurized, the stream has a high penetrating force and serves to dislodge debris and to otherwise cleanse the area under treatment in a manner conducive to healing.

Also an object of this invention is to provide an instrument which is adapted selectively to produce an activated jet of pure oxygen or an atomized jet in which oxygen is intermingled with a liquid having therapeutic properties, or a jet of the liquid, per se, whereby the instrument may be set to afford a jet appropriate to the region being treated.

Still another object of this invention is to provide a low-cost instrument which is simple to operate and which functions efficiently and reliably to carry out oxygenation and cleaning procedures.

Briefly stated, these objects are attained in an instrument including a magnetostrictor or other ultrasonic transducer having a nozzle attached thereto, the nozzle being operatively coupled by a flexible tube to a pressurized tank of medical oxygen. The oxygen flow from the tank is regulated to provide a steady stream of oxygen at a predetermined pressure level.

The nozzle which preferably has a form similar to that of a hypodermic needle, is subjected to high-frequency vibration, the vibrations being imparted to the oxygen flowing therethrough to render the emitted jet highly reactive. An atomizer may be interposed between the oxygen regulator and the nozzle to intermingle with the oxygen a liquid having desired therapeutic properties. A control valve is provided to vary the ratio of oxygen to liquid or to restrict the output either to oxygen or to liquid.

OUTLINE OF THE DRAWINGS

For a better understanding of the invention as well as other objects and further features thereof, reference is made to the following detailed description to be read in conjunction with the accompanying drawings, wherein.

Figure 3:
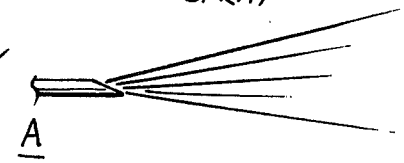
Figure 4:
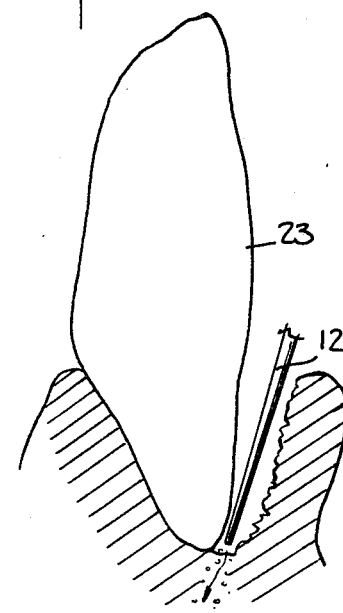
Figure 5:
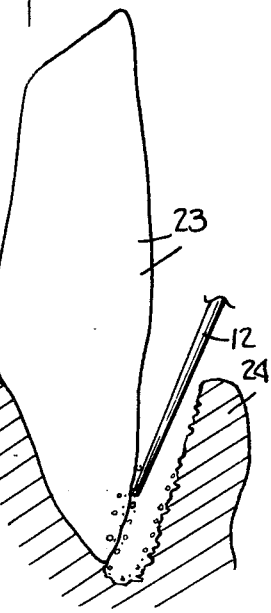

FIGS. 3 A, B and C show the three spray configurations which may be produced by the instrument;

FIG. 4 illustrates one manner of using the instrument;

FIG. 5 shows another manner of using the instrument; and

Figure 6:
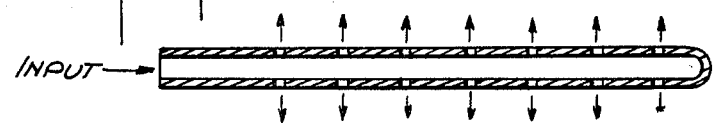

FIG. 6 shows a modified form of nozzle.

DESCRIPTION OF THE INVENTION

Figure 1:
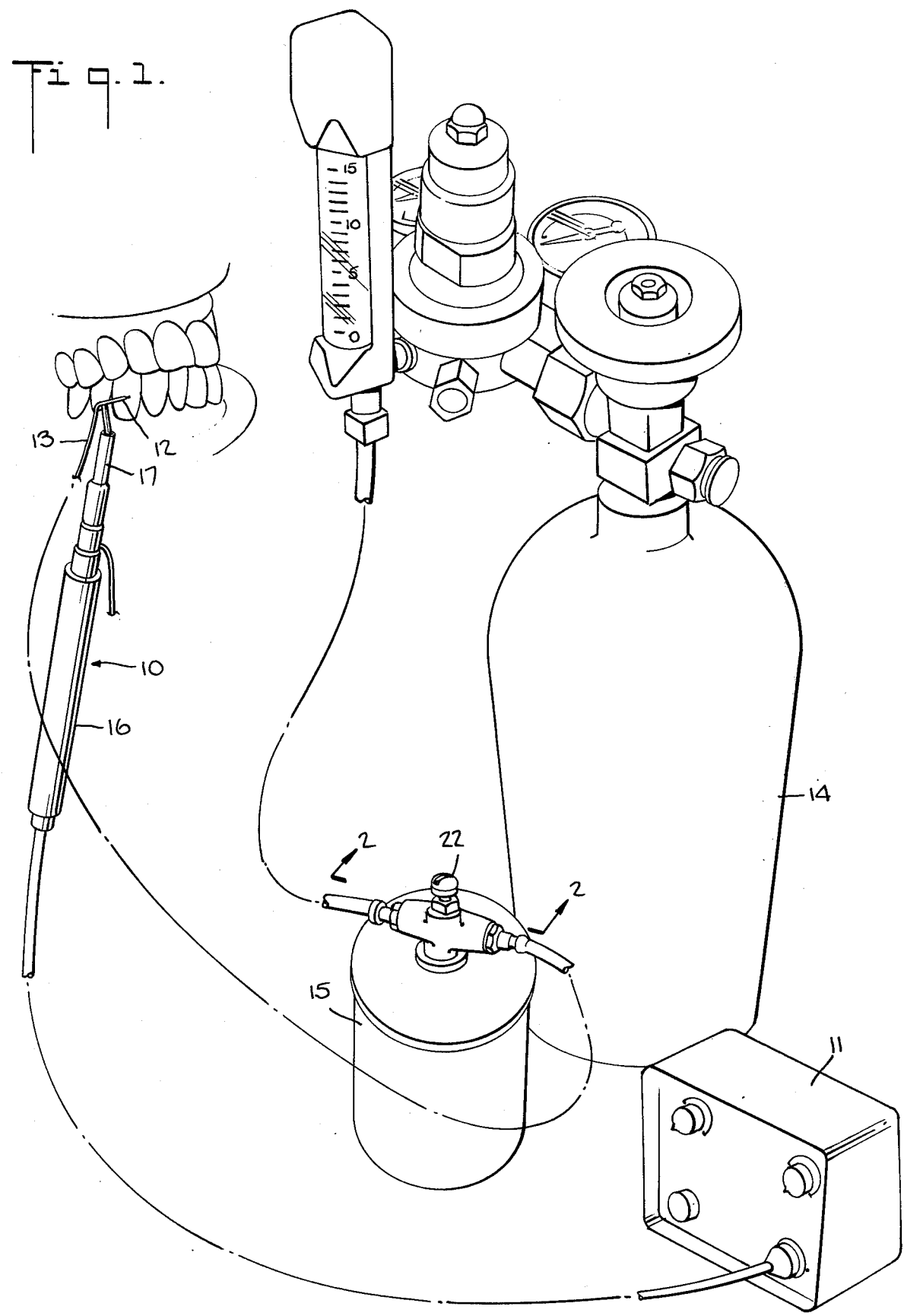
FIG. 1 is a perspective view of an ultrasonic instrument in accordance with the invention.

Referring now to the drawing and more particularly to FIG. 1, there is shown an instrument in accordance with the invention, the instrument including a hand-held electro-mechanical ultrasonic transducer, generally designated by numeral 10 which is energized by a high-frequency generator 11. Attached to the transducer is a nozzle 12 which is coupled by a flexible tube 13 to a tank 14 containing pressurized medical oxygen, an atomizer 15 being interposed between the nozzle and the tank.

Transducer 10 is preferably in the form of a magnetostrictor enclosed within a cylindrical handpiece 16, the magnetostrictive element having an axial extension 17 which is welded or otherwise attached to one side of nozzle 12. In practice, the magnetostrictor may be water cooled. Nozzle 12 is preferably in the form of a standard stainless steel hypodermic needle which may be of a gauge in the 18 to 23 range. Alternatively, the needle may be in the form of a hull so that as it is moved along a tooth surface, it acts as a debriding instrument as well as a nozzle emitting exploding, imploding and bubble-bursting solutions.

The coil surrounding the magnetostrictive element is connected to generator 11 which is an electronic oscillator operated from a 115 V. 60 cycle power line to produce a high-frequency voltage preferably in a range of 20 to 28 KHz. Commercially-available ultrasonic units may be used for this purpose, such as Cavitron model 660 or Ultrason model 880, the magnetostrictors of the units being modified to include a properly-angled nozzle in lieu of a vibrating tip.

Mounted above high-pressure oxygen tank 14 is a pressure regulator 18 provided with a pressure indicator 19, the output pressure being suitably reduced to provide a steady stream of oxygen, preferably at a pressure of about 30 psi. The oxygen must of course be of a purity acceptable for medical and dental applications.

Figure 2:
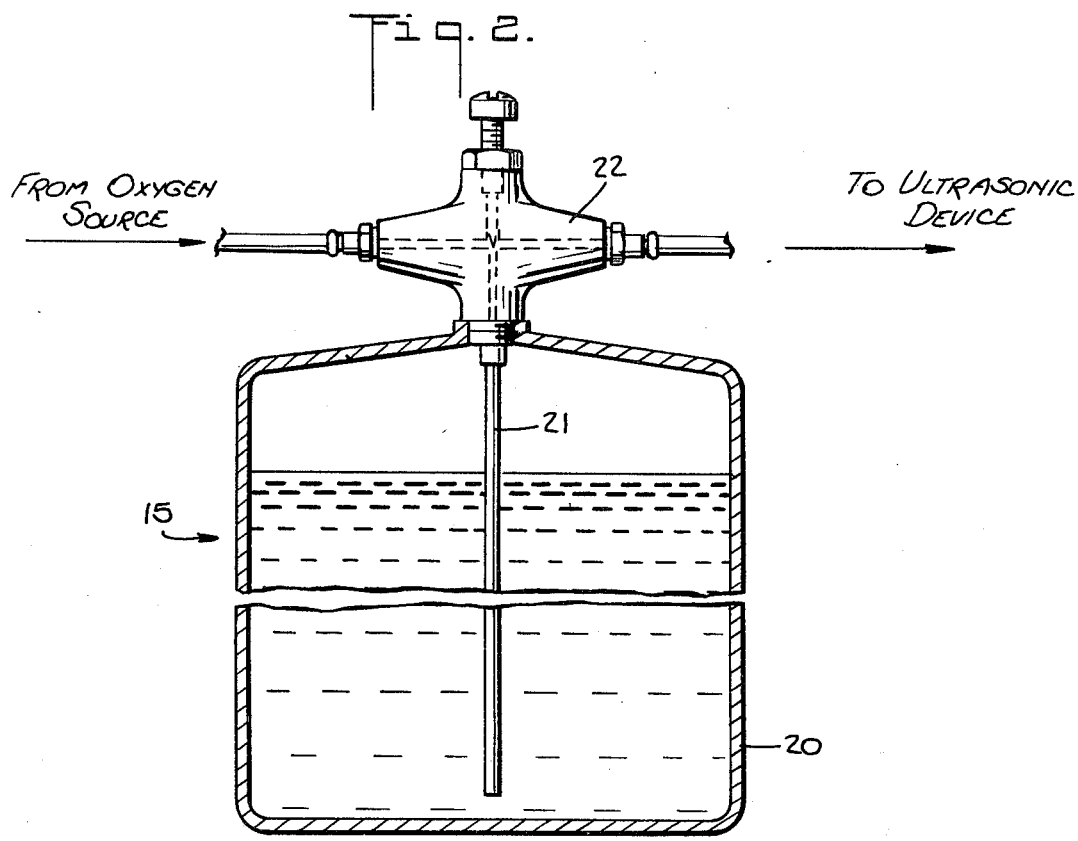
FIG. 2 is a section of the atomizer taken in the plane as indicated by lines 2—2 in FIG. 1.

Atomizer 15 is in the form of a container 20, as shown separately in FIG. 2, having a tube 21 inserted therein, the tube depending from a T-coupling 21 having a control valve providing three operative positions. In one position, the atomizer is by-passed whereby pure oxygen is conveyed to the nozzle whereas in the second position, oxygen flow is blocked and only the liquid drug contained in the atomizer is fed to the nozzle. In the third position, the oxygen is intermingled with the liquid in a dilution depending on the valve setting. Any standard selective valve may be used for this purpose, the details thereof forming no part of the present invention.

FIG. 3 shows the three types of jet sprays emitted by the nozzle. In FIG. 3A, the spray is fluid only, in FIG. 3B the spray is pure oxygen, while in FIG. 3C the fluid and oxygen are intermingled.

As illustrated in FIG. 4, the nozzle may be inserted by the operator in a crevice between the tooth 23 and its adjacent tissue 25 to aerate or oxygenate the crevice, calculus on the surface of the tooth being removed. The gas pressure produced by the jet acts to blow debris and dead tissue out of the crevice and to thoroughly cleanse the area being treated. The activated oxygen delivered to this area reacts with and oxygenates bacteria, spores, protozoa and like material to promote healing at a rapid rate.

The body liquids in the crevice maintain the activated oxygen injected therein in bubble form, the bubbles being minute and separated from each other to optimize their effective surface area. Because of cavitation effects produced by the ultrasonically-activated bubbles, the bubbles burst, releasing shock waves to carry out highly effective cleansing and oxygenation actions. The nozzle, when properly shaped, is capable of also functioning as a vibrating tip and this tip may be applied to the surface of tooth 23, as shown in FIG. 5, to carry out the usual functions of an ultrasonically-vibrated tip as described in the above-identified Ewen and Glickstein text.

The needle, rather then being in the usual hypodermic form, may be constructed as shown in FIG. 6 in the form of a tubular probe 25 of small gauge whose free end is closed but whose sides are foraminated to provide an array of lateral openings from which the oxygen or oxygen-liquid mixture is emitted to create a shower irradiating the site being treated. This shower is useful in cleaning and treating small and normally inaccessible passages and cavities.

The foraminated probe may be made of a sterile rigid plastic of high-strength, such as polycarbonate. It may also be used for delivering oxygen and medications to the internal portions of the bladder, to the penis, or to the interior of the ear.

In the field of periodontics, as noted previously, the instrument is capable of delivering to the site being treated, activated oxygen or an activated liquid medication, or mixtures thereof. The needle-type nozzle makes it feasible to introduce the jet stream within a dental crevice and to move the needle up and down as well as side to side, thereby bathing the entire site under the gum line with fresh oxygen and liquid medication.

In practice, instead of placing the needle outside of the gum to treat the surface thereof, it may be used to pierce the gingiva to inject oxygen directly into the tissue. Where the needle is used for injection, the transducer is provided with a holder thereof which makes it readily possible to remove and replace the needle.

Among the drugs that may be beneficially used in conjunction with oxygen or alone are potassium permanganate which is an oxidizing agent, hydrogen peroxide, sodium hypochlorate or sodium chloride solutions. One can also dissolve antibiotics such as tetracycline in saline solutions and project or spray these ultrasonically-activated atomized solutions into dental crevices. Even when the antibiotic is in insoluble colloidal powder form, it may be dispersed in a suitable liquid carrier for delivery through the nozzle without clogging the nozzle, in that the vibratory action prevents clotting of the powder. The fact that the nozzle, because of the heat developed by the transducer associated therewith runs fairly hot is not a drawback, for the warmth imparted to the jet stream is often helpful in promoting cleansing and oxygenation activity.

Another application for the ultrasonically-vibrating needle-like nozzle is in anesthesia. Current procedures involve either general anesthesia or local infiltration with a hypodermic needle. By the use of an ultrasonically-vibrating needle, one may inject a suitable agent such as xylocaine, procaine or any other acceptable local anesthetic in a dilute solution into the tissue, the vibrating needle facilitating penetration and enhancing the effect of the agent. Similar procedures using an ultrasonically vibrating hypodermic needle may be employed to inject and dissolve clots or to decalcify stones with a decalcifying solution. In all instances the vibrating nozzle serves to produce a jet stream whose constituents are ultrasonically-agitated to render the constituents more effective or reactive.

While there has been shown and described preferred embodiments of an ultrasonic oxygenation instrument in accordance with the invention, it will be appreciated that many changes and modifications may be made therein without, however, departing from the essential spirit thereof.

I claim:

1. An ultrasonic oxygenation instrument for the treatment of diseased tissue or other sites requiring treatment, said instrument comprising:
    (A) an ultrasonic transducer having a nozzle attached thereto, whereby when the transducer is energized, the nozzle is caused to vibrate at an ultrasonic rate;
    (B) a high-frequency generator connected to said transducer to energize same;
    (C) a pressurized source of oxygen of a purity which is medically acceptable:
    (D) an atomizer containing liquid; and
    (E) means coupling said source to said nozzle through said atomizer to feed oxygen intermingled with said liquid thereto, whereby oxygen intermingled with liquid passing through said vibrating nozzle and emitted therefrom as a jet is ultrasonically activated to render it highly reactive with said tissue.

2. An instrument as set forth in claim 1, wherein said nozzle is a hypodermic-type needle.

3. An instrument as set forth in claim 1 wherein said nozzle is a tube whose free end is enclosed, the tube having side openings to produce lateral jets of oxygen intermingled with liquid.

4. An instrument as set forth in claim 2 wherein the needle is formed to provide a tooth-engaging surface whereby said needle acts as a vibrating tip as well as a nozzle.

5. A method of treatment comprising the steps of generating ultrasonic vibrations, imparting said vibrations to a jet stream derived from a source of medically pure oxygen under pressure intermingled with liquid to activate same to an extent imparting thereto therapeutic properties comparable to that of nascent oxygen, and directing said activated stream onto diseased tissue or other surface in need of treatment to oxygenate same.

6. An ultrasonic oxygenation instrument for the treatment of diseased tissue or other sites requiring treatment, said instrument comprising:
    (A) an ultrasonic magnetostriction transducer having a nozzle attached thereto, whereby when the transducer is energized, the nozzle is caused to vibrate at an ultrasonic rate;
    (B) a high-frequency generator connected to said transducer to energize same;
    (C) a pressurized source of oxygen of a purity which is medically acceptable, said source being constituted by a tank having a pressure regulator and indicator to provide a steady stream of oxygen at a predetermined pressure level;
    (D) an atomizer containing liquid; and
    (E) means coupling said source to said nozzle through said atomizer to feed oxygen intermingled with said liquid thereto, whereby oxygen intermingled with liquid passing through said vibrating nozzle and emitted therefrom as a jet is ultrasonically activated to render it highly reactive with said tissue.

7. An instrument as set forth in claim 6, wherein said magnetostrictor is constituted by a magnetostrictive element enclosed in a cylindrical handpiece, the element having an axial projection attached to one side of said nozzle.

* * * * *